(12) United States Patent
Boyde

(10) Patent No.: US 7,118,545 B2
(45) Date of Patent: Oct. 10, 2006

(54) WOUND DRESSING RETAINER AND FASTENING DEVICE

(76) Inventor: Sandra M. Boyde, 644 Engle Rd. Ext., Industry, PA (US) 15052

( * ) Notice: Subject to any disclaimer, the term of this patent is extended or adjusted under 35 U.S.C. 154(b) by 0 days.

(21) Appl. No.: 10/964,359

(22) Filed: Oct. 13, 2004

(65) Prior Publication Data

US 2005/0107732 A1 May 19, 2005

Related U.S. Application Data

(60) Provisional application No. 60/511,065, filed on Oct. 14, 2003.

(51) Int. Cl.
*A61F 13/00* (2006.01)
*A61F 15/00* (2006.01)

(52) U.S. Cl. ............................. 602/79; 602/53; 602/54; 602/58; 602/43

(58) Field of Classification Search .................. 602/79, 602/41, 42, 43, 48, 53, 54, 58; 128/887, 128/888
See application file for complete search history.

(56) References Cited

U.S. PATENT DOCUMENTS

| | | | |
|---|---|---|---|
| 2,012,755 A * | 8/1935 | Otto | 606/217 |
| 2,632,443 A * | 3/1953 | Lesher | 128/888 |
| 4,263,906 A * | 4/1981 | Finley | 602/79 |
| 4,399,816 A * | 8/1983 | Spangler | 128/888 |
| 4,641,641 A * | 2/1987 | Strock | 128/846 |
| 4,732,146 A | 3/1988 | Fasline et al. | |
| 4,972,829 A * | 11/1990 | Knerr | 602/52 |
| 5,000,741 A | 3/1991 | Kalt | |
| 5,060,662 A * | 10/1991 | Farnswoth, III | 128/888 |
| 5,086,763 A * | 2/1992 | Hathman | 602/42 |
| 5,244,523 A | 9/1993 | Tollini | |
| 5,377,695 A * | 1/1995 | An Haack | 128/888 |
| 5,449,340 A * | 9/1995 | Tollini | 602/58 |
| 5,456,660 A | 10/1995 | Reich et al. | |
| 5,562,107 A * | 10/1996 | Lavender et al. | 128/888 |
| 5,580,346 A * | 12/1996 | Spier | 602/42 |
| 5,702,356 A * | 12/1997 | Hathman | 602/41 |
| 5,788,660 A | 8/1998 | Resnik | |
| 5,843,025 A * | 12/1998 | Shaari | 602/53 |
| 5,947,917 A | 9/1999 | Carté et al. | |
| 6,005,159 A * | 12/1999 | Spier | 602/42 |
| 6,043,408 A * | 3/2000 | Geng | 602/58 |
| 2003/0009122 A1* | 1/2003 | Veras | 602/42 |
| 2005/0148921 A1* | 7/2005 | Hsu | 602/48 |

* cited by examiner

*Primary Examiner*—Henry Bennett
*Assistant Examiner*—Amanda Wieker
(74) *Attorney, Agent, or Firm*—The Webb Law Firm

(57) ABSTRACT

An external wound dressing retainer includes a frame having an opening substantially surrounded by the frame, wherein the opening is bounded by a plurality of edges, wherein the frame includes a first side and a second side including an adhesive for adherence to skin of a patient; a flap having a plurality of edges, wherein the dimensions of the flap substantially correspond to the dimensions of the opening, and the flap is attached to the frame via a corresponding edge of the flap and the frame; and a sealing mechanism for releasably engaging non-attached edges of the flap to corresponding non-attached edges of the frame. The sealing mechanism is a zipper arrangement that includes complementary interlocking first and second grooves situated on the non-attached edges of the flap and the frame, respectively, further comprising a sliding element adapted to sealably join the first groove to the second groove.

11 Claims, 4 Drawing Sheets

WOUND DRESSING RETAINER AND FASTENING DEVICE

CROSS REFERENCE TO RELATED APPLICATIONS

This application claims the benefit of U.S. Provisional Patent Application No. 60/511,065, filed Oct. 14, 2003, and entitled "Adhesive Wound Dressing Protective Cover and Retainer", the contents of which are incorporated herein by reference.

BACKGROUND OF THE INVENTION

1. Field of the Invention

The present invention is directed to a wound dressing retainer and, more specifically, to a water and contaminant resistant reusable would dressing retainer.

2. Description of Related Art

Wound dressings generally include an opaque backing layer having an adhesive applied to one side for adhering to the skin. A protective layer, typically made of a release paper is applied to the adhesive side of the backing layer and is releasable therefrom when the wound dressing is applied to the skin. The area immediately covering the wound often has a gauze pad for protecting the wound. The replacement of the gauze pad necessitates removal of the entire wound dressing, including the adhesive side from an individual's skin. When wound dressings are used independent of an integrated adhesive, separate adhesive tape is necessary to secure the wound to the individual's skin. Again, the adhesive only serves the function of holding a particular wound dressing, which necessitates removal of the adhesive when removing or exchanging the wound dressing. Thus, the use of adhesive tape for use in securing wound dressings has long presented a major problem for patients and medical practitioners. Removal of the wound dressing often necessitates replacing the old wound dressing with a new one, which can be stressful to the individual. As seen with many geriatric patients, frequent dressing changes, or even a few dressing changes for patients with thin, fragile skin, can cause serious damage to the skin surrounding the wound.

Wound dressings and dressing retainers to overcome the aforementioned problem have been developed over the years with limited success. Previous designs have exhibited different approaches to securing the dressing. For example, a lace up binder (e.g., Montgomery straps) holds a dressing in place via parallel strips of adhesive having eyelets, wherein each strip is placed on either side of a wound as the dressing is placed in the middle, and laces are laced through the eyelets of the strips. The use of such as dressing retainer has been limited mostly to large abdominal wounds, and is therefore, not as practical for use on smaller wounds or wounds situated on extremities. Other types of dressing retainers designed for use on various areas of the body, allow for easy access to the wound for frequent changes of the dressing. However, protecting the wound site and dressings from contamination is more an issue with these designs than with the Montgomery straps, or elastic band type retainers. Furthermore, none of the prior art wound dressing retainer designs protect outer garments or bedding from drainage of the wound outward through the primary dressing. It is known that wounds that require frequent (e.g., many times a day) dressing changes experience heavy drainage that can saturate and penetrate through primary dressings.

It is, therefore, desirable to overcome the above problems and others by providing a wound dressing retainer that protects the wound and primary dressing from outside contamination, such as feces, urine, or other liquids, protects the environment external from the wound from drainage thereof, and eliminates or reduces the damage and/or irritation caused to the skin from constant replacement of the wound dressing.

SUMMARY OF THE INVENTION

Accordingly, I have invented a wound dressing retainer including a frame having an opening substantially surrounded by the frame, wherein the opening is bounded by a plurality of edges, and wherein the frame includes a first side and a second side including an adhesive for adherence to skin of a patient. The wound dressing retainer further includes a flap having a plurality of edges, wherein the dimensions of the flap substantially correspond to the dimensions of the opening, and the flap is attached to the frame via a corresponding edge of the flap and the frame. A sealing mechanism for releasably engaging non-attached edges of the flap to corresponding non-attached edges of the frame is also included in the wound dressing retainer. Specifically, the sealing mechanism is a zipper arrangement that includes complementary interlocking first and second grooves situated on the non-attached edges of the flap and the frame, respectively. A sliding element is adapted to sealably join the first groove to the second groove, thereby providing a water resistant seal between the frame and the flap. An alternative embodiment wound dressing retainer is also disclosed having dual flaps that may be secured to the frame via raised bars on the frame.

The wound dressing retainer provides access to the wound bed, allowing frequent changes of the primary and or secondary dressings used in the treatment of a wound, without damage to surrounding tissue. Furthermore, primary and optional secondary dressing contained within the wound dressing container are protected from possible outside contamination by bodily fluid or other sources. The wound dressing retainer may be utilized in any moisture prone bodily area, such as an area of incontinence. Additionally, the wound dressing retainer may be utilized in a variety of moisture prevalent environments, such as a shower. These benefits can be realized through cost savings in dressings, increased healing rate, less labor or over-time, and decreased risk of infection.

Still other desirable features of the invention will become apparent to those of ordinary skill in the art upon reading and understanding the following detailed description, taken with the accompanying drawings, wherein like reference numerals represent like elements throughout.

DETAILED DESCRIPTION OF THE INVENTION

Figure 1:
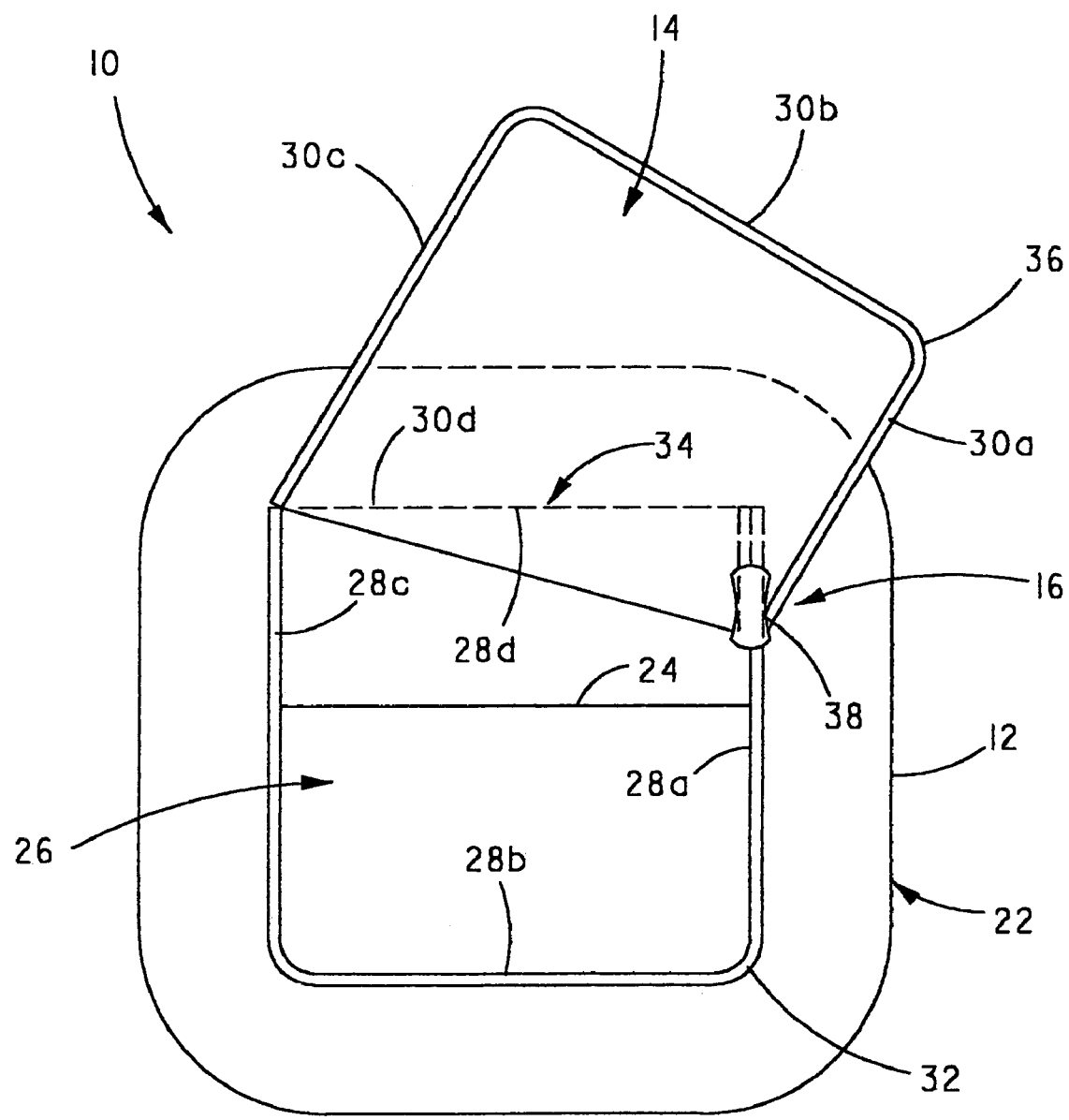
FIG. 1 is a top view of a wound dressing retainer in accordance with the present invention.

For purposes of the description hereinafter, spatial or directional terms shall relate to the invention as it is oriented in the drawing figures. However, it is to be understood that the invention may assume various alternative variations, except where expressly specified to the contrary. It is also to be understood that the specific apparatus illustrated in the attached drawings, and described in the following specification, is simply an exemplary embodiment of the invention. Hence, specific dimensions and other physical characteristics related to the embodiments disclosed herein are not to be considered as limiting.

Figure 2:
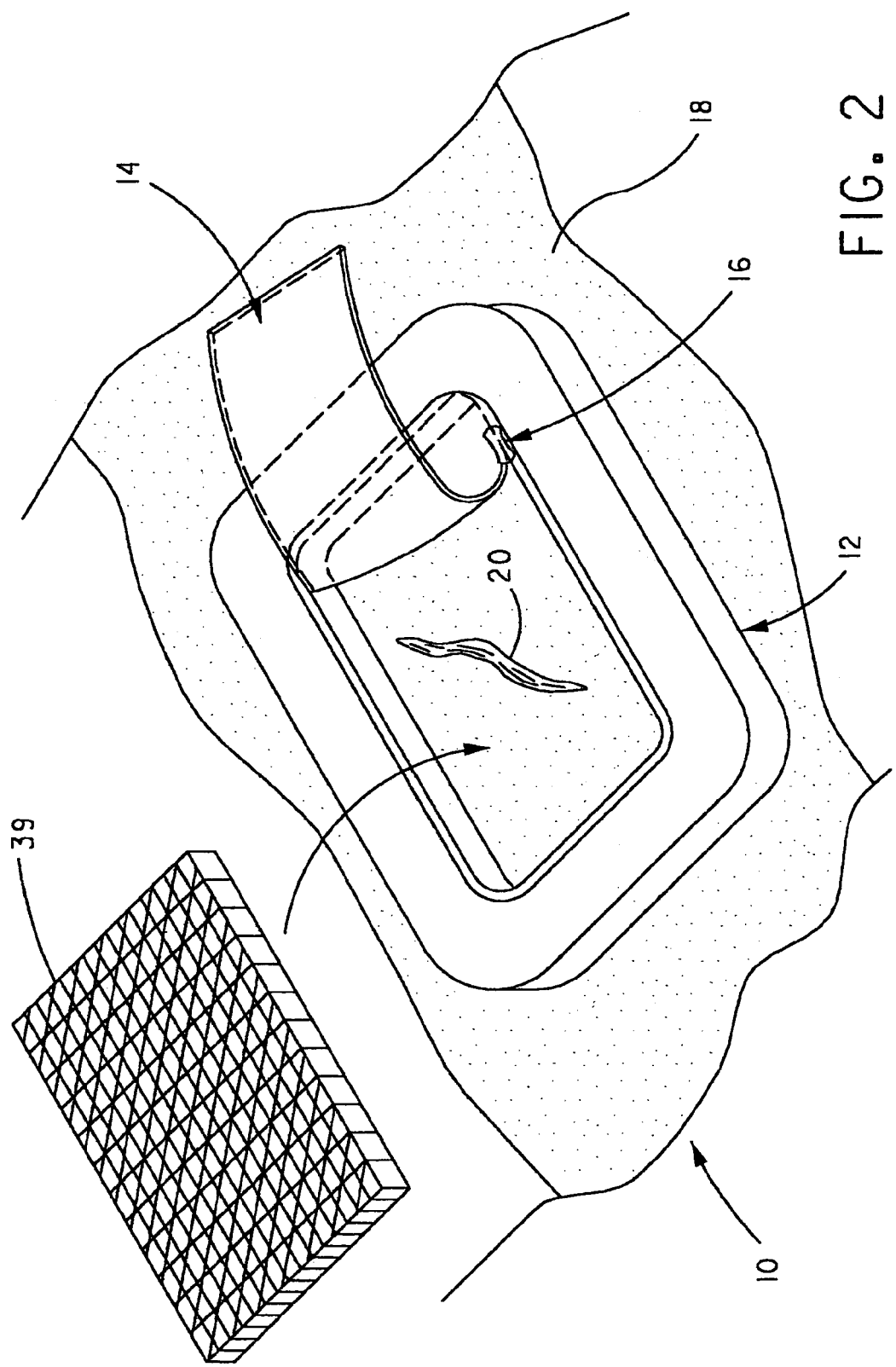
FIG. 2 is a perspective view of the wound dressing retainer of FIG. 1 on an individual in accordance with the present invention.

FIGS. 1 and 2 show a wound dressing retainer 10 that includes a frame 12, a flap 14, and a sealing mechanism 16 situated on an individual's skin 18 having a wound 20 thereon. Frame 12 is desirably constructed of a soft or semi-rigid, but flexible and elastic material, such as foam. Desirably, this material is conducive to applying wound dressing retainer 10, regardless of the contoured surface on an area of the individual's body. An exemplary material includes, but is not limited to a hydropolymer foam having a silicone coating. Additionally, frame 12 may be latex free and hypoallergenic, allowing wound dressing retainer 10 to be applied to the greatest number of individuals without concern of adverse reactions. The surfaces of frame 12 configured not to be in contact with the individual, may be coated with a material that acts as a protective barrier to frame 12 and to facilitate efficient cleaning thereof. For example, the coating may include, but is not limited to silicone, rubber, plastic, or a composite material that is impermeable to liquids. Thus, frame 12 may easily be cleaned and sanitized between dressing changes of any accumulated drainage, puss, or other exudates. Due to the non-absorbent coating, alcohol wipes or other suitable medical cleaning solutions may be utilized for efficient and effective cleaning thereof.

Frame 12 includes an adhesive portion 22, such as a backing, that is adapted to be adhered to skin 18 of the individual. It is to be understood that any conventional adhesive which is non-toxic and readily adheres to the skin may be utilized. For example, suitable commercial adhesives specific for skin adhesion include, but are not limited to MeFix® by Mölnlycke Health Care AB, Hypafix® by Smith & Nephew, or a hydrocolloid type of adhesive, such as DuoDERM® by ConvaTec. It is to be understood that these and other types of adhesives are intended to provide a waterproof seal between frame 12 and skin 18. Adhesive portion 22 may be covered with a release paper 24 which protects adhesive portion 22 during storage of wound dressing retainer 10. Adhesive portion 22 may be easily released therefrom when wound dressing retainer 10 is to be placed over wound 20. It is to be understood that release paper 24 may be any suitable sheet material having properties including, but not limited to that of paper, polyethylene, and/or polypropylene.

Frame 12 is desirably rectilinear in shape, assuming either a square or a rectangular shape is utilized. However, it is to be understood that frame 12 may embody any suitable shape, as the shape does not limit the invention. A central opening 26 is defined within frame 12, wherein opening 26 is bounded by a plurality of edges 28a–d. It is to be understood that more or less edges than edges 28a–d may bound opening 26 if an alternative shape is selected for frame 12. Desirably, edges 28a–c define a groove 32, however, alternatively, edges 28a–c may define a tongue. Desirable sizes for opening 26 include, but are not limited to, 2"×2"; 4"×4"; 4"×6"; 5"×9"; and 8"×10". The depth of opening 26 is determined by the depth dimension of frame 12, as opening 26 extends completely through frame 12. Desirably, the distance from an inner portion of frame 12 defined by any one of edges 28a–d to an outer periphery of frame 12 is at least one inch. It is to be understood that the measurements described herein are for exemplary purposes only, thereby allowing wound dressing retainer 10 to assume other non-explicitly described dimensions that may be better suited for a particular application of wound dressing retainer 10.

Flap 14 is sized to cover opening 26 and, more specifically, the dimensions of flap 14 correspond to the dimensions of opening 26. Flap 14 includes a plurality of edges 30a–d. Flap 14 is attached to frame 12, either as a separate or continuous piece, via a corresponding edge of flap 14 and frame 12. For example, edge 30d of flap 14 is attached to edge 26d of frame 12. Thus, flap 14 may pivot along crease 34 defined by edge 30d and edge 26d to allow flap 14 to be selectively movable from a closed position covering opening 26 to an open position whereupon opening 26 is uncovered. Edges 30a–c are therefore unattached to frame 12. Similar to the edges 28a–c of frame 12, edges 30a–c of flap 14 also define a groove 36. Grooves 32 and 36 are adapted to complementarily interlock with one another, so that flap 14 may be sealably joined to frame 12. Specifically, non-attached edges 30a–c of flap 14 in the open position, may be attached to edges 28a–c of frame 12 when flap 14 is in the closed position.

The sealing of flap 14 to frame 12 is effected by movement of sealing mechanism 16. Specifically, sealing mechanism 16 may be embodied in a variety of functional equivalents, including the zipper arrangement depicted in FIGS. 1 and 2. It is to be understood that sealing mechanism 16 is operated in conjunction with the type of complementary connection or attachment configuration utilized by edges 28a–c and edges 30a–c. For example, the zipper arrangement includes a sliding element, such as a tab 38, that includes two channels (not shown) for accommodating corresponding portions of grooves 32 and 36 therein. The sliding element may be any other suitable grip or hold accommodating sliding element. For example, tab 38 may include a ridged surface, a tapered surface, a pull cord, or any other structure that is conducive for a user to grasp and pull tab 38. The channels of tab 38 are configured to interlock the grooves as tab 38 moves along edges 28a–c and edges 30a–c. Thus, after having moved tab 38 along the unattached portions of frame 12 and flap 14, sealing mechanism 16 sealably joins frame 12 to flap 14. The sealing fundamentals described in regard to the aforementioned zipper arrangement are relatively embodied in what is commonly known as a Ziploc® brand sealable bag. However, it is to be understood that the zipper arrangement of the present invention desirably provides a water-resistant seal between edges 28a–c and edges 30a–c. An exemplary zipper arrangement for providing a water-resistant seal is incorporated into a water-proof navigation chart holder sold by Binnacle Navigation Instruments of Nova Scotia Canada. Other types of sealing mechanisms for edges 28a–c and edges 30a–c include, but are not limited to an interlocking tongue and groove arrangement, resusable adhesive, magnets or magnetic strips, clamps, and a traditional zipper with offset engaging elements. It is to be understood that frame 12 of wound dressing retainer 10 may be of thick enough construction so that the tab 38 or any equivalent thereof, is situated below the surface of frame 12, thereby reducing the possibility of friction irritation for the individual or the snagging by an object coming into contact with wound dressing retainer 10. Flap 14 may be constructed of similar material as that of frame 12, however, as flap 14 is desirably thinner than frame 12 and is subjected to greater handling than frame 12, flap 14 may be constructed of a bendable plastic material, such as thin vinyl sheet. Regardless of the material utilized in the construction of flap 14, it is desirable that flap 14 is a non-absorbent material and/or is coated with a material that facilitates efficient cleaning thereof, similar to the surfaces of frame 12 configured not to be in contact with the individual. Flap 14 may include elastic or stretch properties that would accommodate dressings of various thicknesses that extend out of opening 26 and beyond the surface of frame 12. Flap 14 may be opaque or transparent, depending on the application of the wound dressing retainer. For example, if a user wishes to observe the amount of exudate absorbed by the underlying dressing, then it is beneficial for flap 14 to be constructed of a transparent material that would allow a status check of the dressing to be made without having to open flap 14. However, for aesthetic purposes, flap 14 may be opaque, so as to hide any unappealing view of the dressing and or wound. With regard to an opaque flap 14, flap 14 may be decorated with various designs and/or illustrations, particularly for younger children.

It is to be understood that any suitable dressing 39 may be utilized with wound dressing retainer 10. Specifically, the basic form of dressing 39 may be reproduced in several different sizes and shapes, to accommodate a wide range of dressing choices for a particular application. Additionally, depending on the depth of frame 12, the amount of dressing 39 inserted into opening 26 may vary. The depth of frame 12, however, does not dictate the amount of dressing 39 that may be utilized, as it may be the case that a highly absorbent dressing 39 requires sufficient expansion room within frame 12. Furthermore, a plurality of dressings 39, such as primary and secondary dressings may be used concurrently with wound dressing retainer 10.

Figure 3:
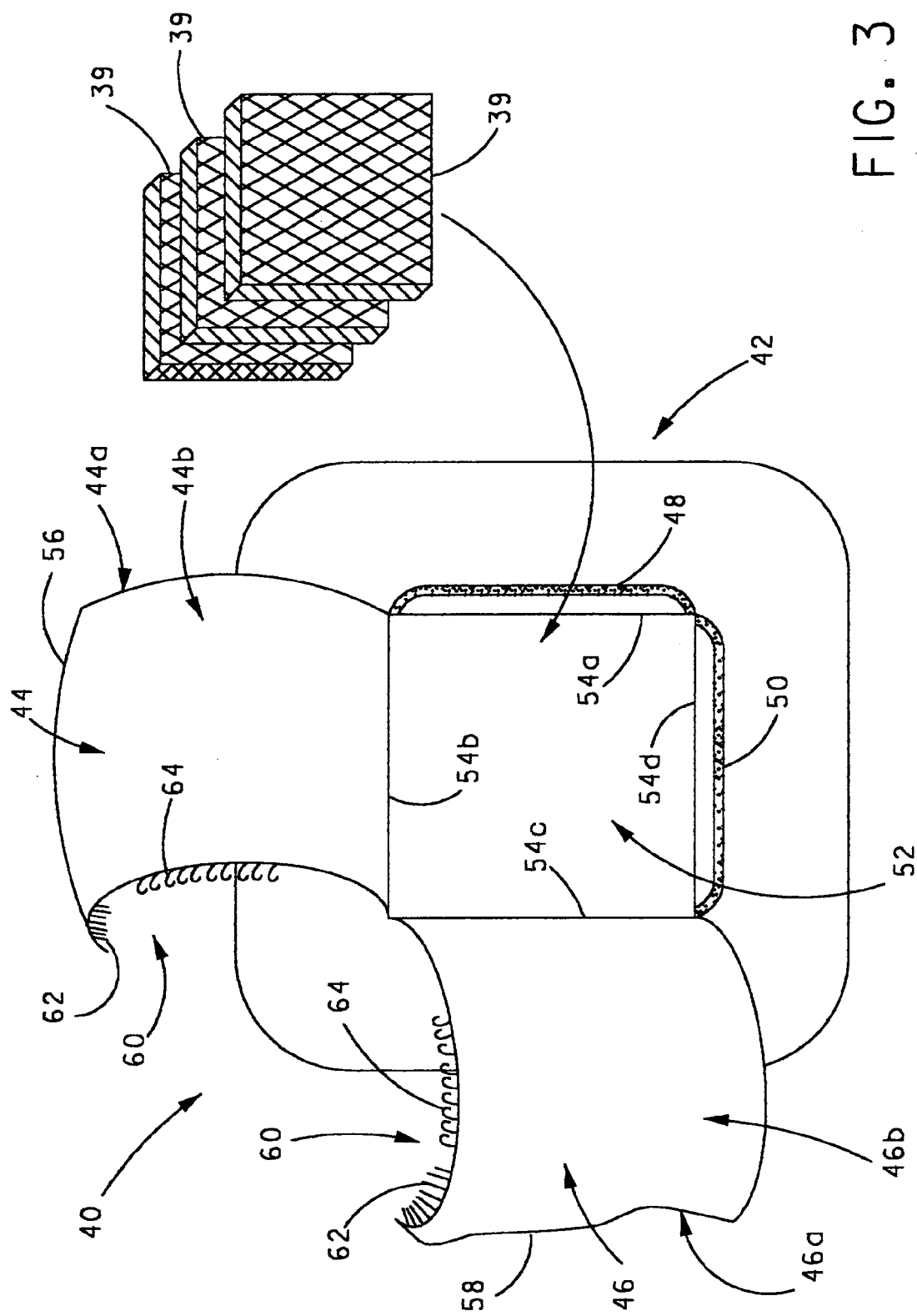
FIG. 3 is a top view of a alternative embodiment wound dressing retainer having flaps in accordance with the present invention.
Figure 4:
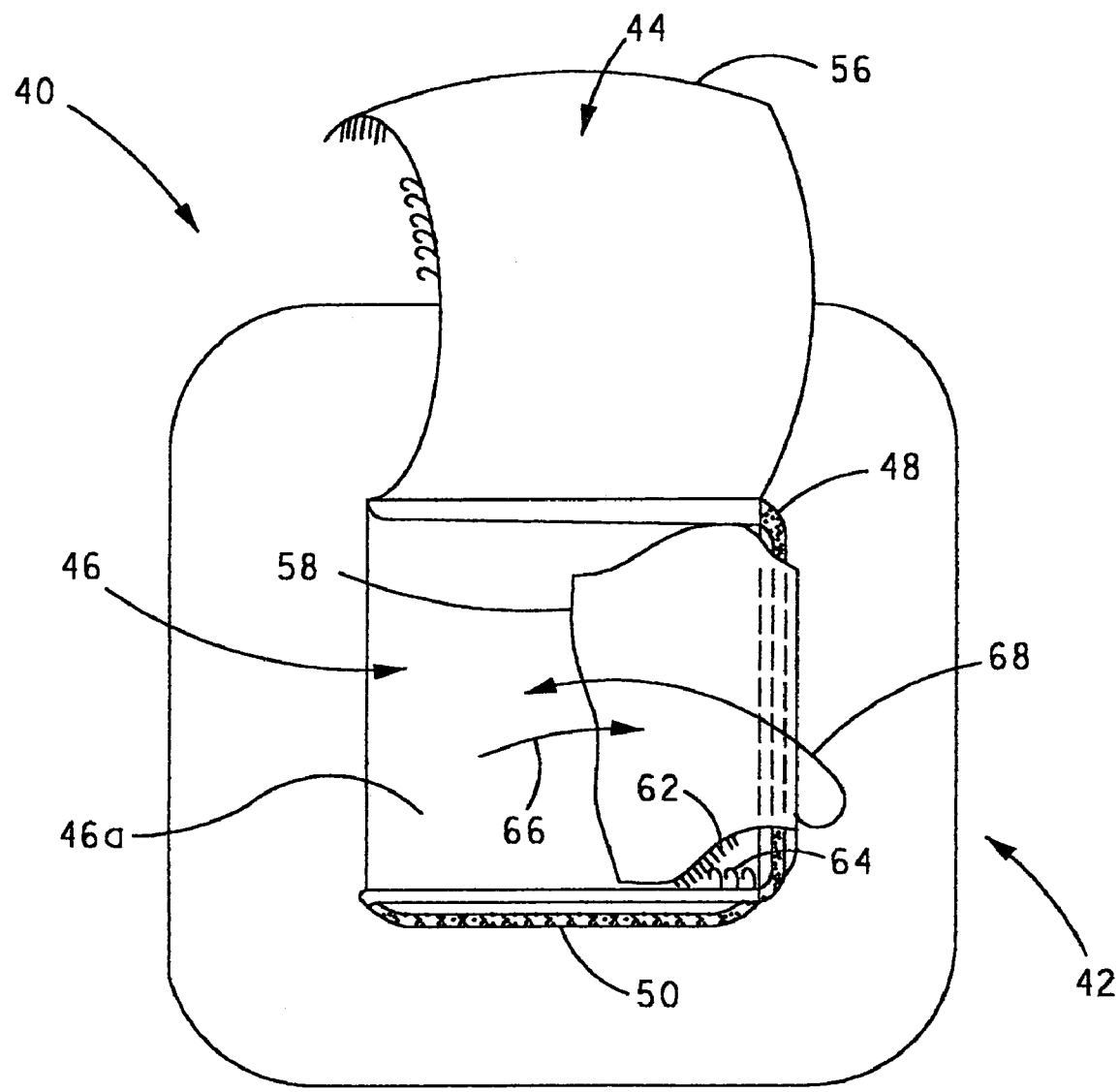
FIG. 4 is a top view of the alternative embodiment wound dressing retainer of FIG. 3 showing the fastening of the flaps thereof.

With reference to FIGS. 3 and 4, and with continuing reference to FIGS. 1–2, an alternative embodiment wound dressing retainer 40 is shown. Alternative embodiment wound dressing retainer 40 includes a frame 42, a first flap 44, a second flap 46, a first raised structure 48, and a second raised structure 50. Frame 42 may be of the same design, construction, and material as that of frame 12 of wound dressing retainer 10. Thus, the exemplary materials discussed in connection with wound dressing retainer 10, may also be applied to wound dressing container 40.

Frame 42 defines a central opening 52 sized to accommodate one or more dressings 39 therein. Frame 42 includes a plurality of edges, such as edges 54a–d, that define opening 52. Edges that are in perpendicular relation to each other, such as edges 54a and 54d, have situated thereon first raised structure 48 and the second raised structure 50, respectively. Desirably, raised structures 48, 50 are plastic bars having sufficient vertical clearance from the surface of frame 42 to accommodate flaps 46, 44, respectively, therethrough. It is to be understood that any suitable raised structure may be substituted for plastic bars 48, 50. For example, an elastic cord or rigid string spanning a distance greater than the width of each of flaps 44, 46 may also be utilized.

Flaps 44 and 46 include front sides 44a and 46a and back sides 44b and 46b, respectively. Desirably, flaps 44, 46 are substantially as wide as the width of opening 52. First flap 44 and second flap 46 are attached to edges oriented on different planes from each other. For example, first flap 44 and second flap 46 are attached in a perpendicular relation to each other, so that one end of first flap 44 is attached to edge 54b and one edge of second flap 46 is attached to edge 54c. Alternatively, edges 54a and 54d may be utilized to also provide first flap 44 with a perpendicular relation to second flap 46. A fastening mechanism is attached to free ends 56 and 58 of first flap 44 and second flap 46, respectively. Desirably, the fastening mechanism includes a Velcro® brand fastener 60, however, it is to be understood that other fastening mechanisms may be utilized including, but not limited to, an adhesive, a tape, a hook and eye closure, a buckle, snaps, and a magnet. The Velcro® brand fastener 60 includes a hook arrangement 62 and a loop arrangement 64 situated on front side 44a of first flap 44 and front side 46a of second flap 46.

First and second flaps 44 and 46 may be closed and secured around plastic bars 50 and 48, respectively, as shown in FIG. 4. Either first flap 44 or second flap 46 is selected to be secured first. For exemplary purposes, second flap 46 is folded in a partially closed position toward plastic bar 48, as indicated by arrow 66. Thereafter, free end 58 of second flap 46 is directed underneath and then over plastic bar 48, in a looped configuration, as indicated by arrow 68. Finally, free end 58 is extended in the opposite direction of arrow 66 and is mated to front side 46a of flap 46 via the fastening of hook arrangement 62 to loop arrangement 64 of Velcro® brand fastener 60. This process is then repeated with the remaining flap, such as first flap 44. Although discussed in the context of two flaps 44, 46, it is to be understood that alternative embodiment wound dressing retainer 40 may also utilize a single flap, such as flap 44 or flap 46. However, use of a single flap does not promote water resistance as much as the use of the dual flap design discussed herein. Flaps 44, 46 desirably include elastic or stretch properties that would accommodate dressings of various thicknesses that extend out of the opening 52 and beyond the surface of frame 12. Additionally, the downward pressure exerted by flaps 44, 46, allows dressing 39 to maintain constant contact with the wound and limit dressing movement.

It is to be understood that alternative embodiment retainer 40 does not necessarily provide a waterproof seal as does wound dressing retainer 10. However, the coating as well as the horizontal/vertical flap configuration will allow water resistant protection. Thus, alternative embodiment retainer 40 is suitable where resistance to water, as well as breathability of the wound is desirable. As discussed with reference to wound dressing retainer 10, the outer surface of frame 42 as well as front sides 44a and 46a and back sides 44b and 46b of flaps 44 and 46, respectively, of alternative embodiment retainer 40 are also desirably constructed of a non-absorbent material and/or are coated with a material that facilitates efficient cleaning thereof.

As discussed, any of the flaps of the present invention may be secured to frame 12 or 42 through alternate mechanisms, including but not limited to adhesive tape, magnets, interlocking grooves, and interlocking tongue and groove configurations. Use of such alternate mechanisms may require modifying the surface of the frame, flaps, or both to accommodate these alternate mechanisms. For example, it is envisioned that an air or liquid actuated tongue and groove locking mechanism may be utilized with the present invention. Specifically, a tongue is situated along the edges of a flap, wherein the tongue is configured to be inserted into a groove integrated into the frame. The groove is surrounded by a channel embedded in the frame, wherein the groove is configured to contract upon expansion of the channel from the force of air or liquid introduced therein. The air or liquid may be introduced into the channel via a LureLock® or other suitable injection port. In effect, the tongue is locked into the channel, thereby providing a water resistant seal between the flap and the frame.

The aforementioned properties of the wound dressing retainer 10 and derivatives thereof are conducive for allowing the wound dressing retainer 10 to remain on the same area of the body for an extended period of time, such as a week. This is in contrast to conventional wound dressings that require daily replacement. Desirably, the components of the wound dressing retainer 10 are effectively and efficiently integrated with one another to provide an optimal balance between functionality, patient comfort, ease of use, and cost per unit.

The invention has been described with reference to the desirable embodiments. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An external wound dressing retainer comprising:
   a flexible frame having an opening substantially surrounded by the frame, wherein the opening is bounded by a plurality of edges, wherein the frame includes a first side and a second side including an adhesive for adherence of the frame to skin of a patient;
   a flexible flap having a plurality of edges, wherein the dimensions of the flap substantially correspond to the dimensions of the opening, and the flap is attached to the frame via a corresponding edge of the flap and the frame; and
   a sealing mechanism for releasably engaging non-attached edges of the flap to corresponding non-attached edges of the frame, wherein the sealing mechanism includes a zipper arrangement having complementary interlocking first and second grooves situated on the non-attached edges of the flap and the frame, respectively, further including a sliding element adapted to sealably join the first groove to the second groove, wherein the sealing mechanism provides a liquid-proof seal between the edges of the flaps and the edges of the frame.

2. The external wound dressing retainer of claim 1, wherein the sliding element further comprises one of a ridged surface and a tapered surface.

3. The external wound dressing retainer of claim 1, further comprising a removable backing affixed to the second side of the frame.

4. The external wound dressing retainer of claim 1, wherein the depth of the frame is sized to accommodate a dressing within the opening of the frame.

5. The external wound dressing retainer of claim 1, wherein the flap is selectively movable from a closed position covering the opening to an open position so that the opening is uncovered.

6. The external wound dressing retainer of claim 1, wherein the adhesive provides a water-resistant seal between the frame and the skin of the patient.

7. The external wound dressing retainer of claim 1, wherein the flap is constructed of non-absorbent material.

8. The external wound dressing retainer of claim 1, wherein the opening is one of 2"×2"; 4Δ×4"; 4"×6"; 5"×9"; and 8"×10" in size.

9. The external wound dressing retainer of claim 1, wherein the frame is substantially rectilinear.

10. The external wound dressing retainer of claim 9, wherein the distance from an inner portion of the frame defined by any of the edges to an outer periphery of the frame is at least one inch.

11. The external wound dressing retainer of claim 1, wherein the frame is constructed of semi-rigid foam material.

* * * * *

UNITED STATES PATENT AND TRADEMARK OFFICE
CERTIFICATE OF CORRECTION

PATENT NO. : 7,118,545 B2 Page 1 of 1
APPLICATION NO. : 10/964359
DATED : October 10, 2006
INVENTOR(S) : Boyde It is certified that error appears in the above-identified patent and that said Letters Patent is hereby corrected as shown below:

<u>Column 8</u>, Line 27, Claim 8, "4 Δx4" " should read -- 4"x4" --

Signed and Sealed this

Twentieth Day of March, 2007

JON W. DUDAS
*Director of the United States Patent and Trademark Office*